United States Patent [19]

Massaroli

[11] 4,224,327
[45] Sep. 23, 1980

[54] 4-PYRIMIDYL SULFIDES FOR THE TREATMENT OF GASTRIC ULCERS

[75] Inventor: Giangiacomo Massaroli, Milan, Italy
[73] Assignee: Poli Industria Chimica S.p.A., Italy
[21] Appl. No.: 6,504
[22] Filed: Jan. 25, 1979

[30] Foreign Application Priority Data

Feb. 2, 1978 [IT]  Italy ............................... 19905 A/78

[51] Int. Cl.$^2$ ................... A61K 31/505; C07D 401/12
[52] U.S. Cl. .................................... 424/251; 544/319; 544/320
[58] Field of Search ................. 544/319, 320; 424/251

[56] References Cited

U.S. PATENT DOCUMENTS 4,117,131   9/1978   Schwender et al. ................. 544/320

Primary Examiner—Paul M. Coughlan, Jr.
Attorney, Agent, or Firm—Michael J. Striker

[57] ABSTRACT

The invention concerns 4-pyrimidyl sulfides of the general formula

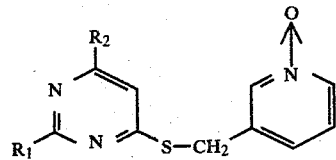

wherein $R_1$ and $R_2$ are the same or different, and are H, $NH_2$ or $CH_3$. The compounds and pharmaceutical compositions containing the compounds, useful for the treatment of gastric ulcers and pathological states relating to gastric hypersecretion, exhibit a low toxicity and high degree of effectiveness.

9 Claims, No Drawings

4-PYRIMIDYL SULFIDES FOR THE TREATMENT OF GASTRIC ULCERS

SUMMARY OF THE INVENTION

This invention is in the field of pharmaceutical compositions and methods for the treatment of gastric ulcers and the pathological states related to gastric hypersecretion.

In particular, the invention concerns a series of 4-pyrimidyl sulfides of the general formula

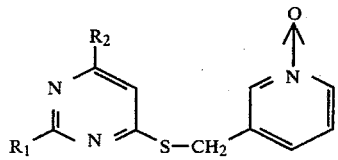

where $R_1$ and $R_2$, which may be the same or different, are H, $NH_2$ or $CH_3$.

The compounds of the invention were studied pharmacologically by determining the $DL_{50}$ by oral administration in mice and rats. In addition, the $DE_{50}$ (effective dose in reducing by 50% the animal pathology) was determined employing the standard methods for screening substances with potential anti-ulcer activity. Carbenoxolone was used for comparison purposes, this compound being well known for its anti-ulcer properties and widely used in human therapy for the treatment of gastric ulcers.

The effective dose comparative determinations were carried out with rats subjected to ligature of the pylorus (Shay rats) in accordance with the method described by Brown et al. in *Arch. Int. Pharmacodyn.* 145: 489 (1963). In addition, the comparison tests were run with test animals with ulcers induced by indomethacin (Lee et al., *Arch. Int. Pharmacodyn.* 191: 370 (1971) and by cold and restraint methods (Senay and Levine, *Proc. Soc. Exp. Biol. Med.* 124: 1221 (1967)).

The results of these experiments are given in Table I.

TABLE I

| SUBSTITUENTS | | $DL^{50}$ mg/kg p.o. | | $DE_{50}$ in mg/kg p.o. | | |
|---|---|---|---|---|---|---|
| R | $R_1$ | mouse | rat | Shay | Indomethacin | cold and restraint |
| H | H | 1400 | 2300 | 2 | 2.4 | 3 |
| $CH_3$ | $NH_2$ | 1600 | 2800 | 9.5 | 21.6 | 4.3 |
| $NH_2$ | $CH_3$ | 1400 | 2200 | 4.2 | 7.9 | 2.1 |
| CARBENOXOLONE | | 1400 | | 30 | 350 | 50 |

In addition to the very low toxicity of the novel compounds, the data shows the marked effectiveness of these compounds, which, depending upon the tests and the substituents, are from 3 to 150 times more active than carbenoxolone.

The compounds may be administered in human therapy in the form of tablets, capsules, bags or packets, either singly or in admixture with known antacids and neutralizing agents, such as aluminum hydroxide, magnesium hydroxide, magnesium trisilicate and tricalcium phosphate. In general, individual dosage units should contain from 25 to 500 mg of the active agent. The preferred daily dosage is about 75 to 1500 mg.

The compounds of the invention may be prepared through the reaction of an alkaline salt of a 4-mercaptopyrimidine of the general formula II, in which $R_1$ and $R_2$ are defined as above, with 3-chloromethylpyridine-N-oxide according to the equation:

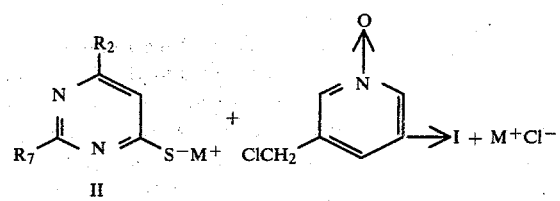

where M is an alkaline metal, preferably sodium.

The reaction of the compounds II with 3-chloromethylpyridine-N-oxide may be carried out in an alcoholic solvent, such as methanol or ethanol, or in a dipolar aprotic solvent, such as N,N-dimethylformamide, within the temperature range of about $-10°$ to $+100°$ C. Alternatively, the reaction may be effected within the temperature range of about $30° - 120°$ C. in aprotic solvents, such as ethers, aromatic hydrocarbons or halogenated derivatives. The reactions are essentially stoichiometric. The salts II may be obtained for example by treatment of the corresponding mercaptopyrimidines obtained through conventional methods with a sodium or potassium alkoxide, preferably sodium methoxide, in a substantially stoichiometric amount.

The structures of the products were confirmed by elemental analysis and by IR and NMR spectroscopy.

The novel features which are considered as characteristic of the invention are set forth in particular in the appended claims. The invention itself, however, together with additional objects and advantages thereof, may be better understood from the following description of specific examples.

EXAMPLE 1

4-(N-oxidopyridyl-3-methyl)thiopyrimidine 11.2 g (0.1 moles) 4-mercaptopyrimidine is dissolved in 100 ml ethanol containing 10.8 g sodium methoxide. 18 g (0.1 moles) 3-chloromethylpyridine-N-oxide hydrochloride is added; the mixture is heated under reflux for about one hours. The solution is cooled to ambient temperature, the sodium chloride filtered off, and the filtrate evaporated under vacuum to eliminate the solvent. The residue is crystallized from ethyl acetate to give 15.35 g of product (M.P.$=105°-108°$ C.; yield$=70\%$).

EXAMPLE 2

2-amino-6-methyl-4-(N-oxide-pyridyl-3-methyl)thiopyrimidine 14.1 g (0.1 moles) 2-amino-6-methyl-4-mercaptopyrimidine is dissolved in 100 ml methanol containing 10.8 g sodium methoxide. 18 g (0.1 moles) 3-chloromethylpyridine-N-oxide hydrochloride is added, and the mixture heated under reflux for about two hours. The solvent is evaporated without filtering off the sodium chloride; the residue is redissolved in a small amount of water, and the aqueous solution saturated with potassium carbonate. The solid which separates out is filtered off and recrystallized from ethanol. 17.85 g of product is obtained (M.P.$=175°-177°$ C.; yield$=72\%$).

EXAMPLE 3

6-amino-2-methyl-4-(N-oxido-pyridyl-3-methyl)thiopyrimidine 14.1 g (0.1 moles) 6-amino-2-methyl-4-mercaptopyrimidine is dissolved in 50 ml dimethylformamide containing 10.8 g sodium methoxide. 18 g (0.1 moles) 3-chloromethylpyridine-N-oxide hydrochloride is added; the mixture is heated to 70° for about three hours. The mixture is cooled and diluted with 100 ml water. The solid which precipitates is filtered off. After crystallization from ethanol, 18.6 g of product is recovered. (M.P.=209°–211° C.; yield=75%)

The invention is not intended to be limited to the examples shown, since various modifications may be made without departing from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A compound of the formula

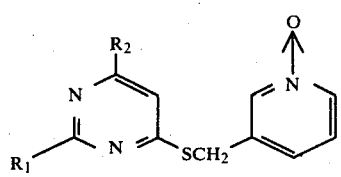

wherein $R_1$ and $R_2$ are the same or different, and are H, $NH_2$ or $CH_3$.

2. A compound as defined in claim 1, comprising 4-(N-oxidopyridyl-3-methyl)-thiopyrimidine.

3. A compound as defined in claim 1, comprising 2-amino-6-methyl-4-(N-oxidopyridyl-3-methyl)thiopyrimidine.

4. A compound as defined in claim 1, comprising 6-amino-2-methyl-4-(N-oxidopyridyl-3-methyl)thiopyrimidine.

5. A pharmaceutical composition for treatment of pathological states related to gastric hypersecretion, comprising 4-pyrimidyl sulfides of the formula

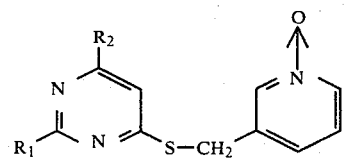

wherein $R_1$ and $R_2$ are the same or different and are H, $CH_3$ or $NH_2$, as active agent, and a second agent, said second agent being inactive.

6. A pharmaceutical composition as defined in claim 5, containing an antacid or neutralizing agent.

7. A pharmaceutical composition as defined in claims 5, or 6 in unit dosage form, containing about 25 to 500 mg of said active agent.

8. A method of treating gastic ulcers or gastric hypersecretion, comprising administering to humans or animals a pharmacologically effective amount of a compound of the formula

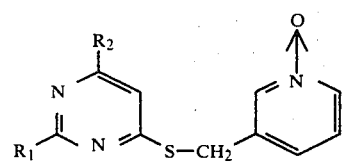

where $R_1$ and $R_2$ are the same or different, and are H, $NH_2$ or $CH_3$.

9. A method as defined in claim 8 for human therapy, wherein said effective amount in discrete daily dosage form is about 75 to 1500 mg.

* * * * *